United States Patent [19]

Orzalesi et al.

[11] 4,226,885
[45] Oct. 7, 1980

[54] GUANYLHYDRAZONES AND MEDICAMENTS CONTAINING THEM

[75] Inventors: Henri Orzalesi; Jean Castel, both of Montpellier, France

[73] Assignee: Choay S.A., Paris, France

[21] Appl. No.: 841,947

[22] Filed: Oct. 13, 1977

[30] Foreign Application Priority Data

Oct. 13, 1977 [FR] France .................. 76 30722

[51] Int. Cl.$^3$ .............. C07C 143/02; C07C 133/10; A61K 31/255; A61K 31/155
[52] U.S. Cl. .................. 424/303; 424/326; 260/564 F; 260/456 A
[58] Field of Search ........ 260/564 F, 456 A; 424/326, 303

[56] References Cited

U.S. PATENT DOCUMENTS

| | | | |
|---|---|---|---|
| 3,130,232 | 4/1964 | Paquette | 260/564 F |
| 3,131,218 | 4/1964 | Spickett et al. | 260/564 F |
| 3,816,531 | 6/1974 | Bruce et al. | 260/564 F |

OTHER PUBLICATIONS

Chemical Abstr., vol. 49, col. 168(e) (1955).
Chemical Abstr., vol. 55, col. 2540(g) (1961).
Mutschler et al., Biochemical Pharmacology, vol. 19, pp. 9-15, (Pergamon Press. 1970).
Morrison & Boyd, "Organic Chemistry", 3rd Ed., pp. 641-643 (1973).

*Primary Examiner*—Bernard Helfin
*Attorney, Agent, or Firm*—Weiser, Stapler, Spivak

[57] ABSTRACT

New guanylhydrazones of phenoxyacetic acid. These guanylhydrazones, also their physiologically acceptable salts, are characterized by the following general formula I in which $R_1$, $R_2$, $R_3$, $R_4$, $R_5$, R and R' have the meanings which are hereinafter described.

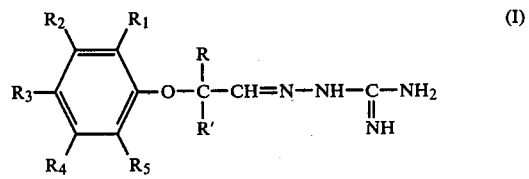

The new guanylhydrazones are useful as medicaments, in particular antimitotic, IMAO and platelet antiagregant activity.

33 Claims, 1 Drawing Figure

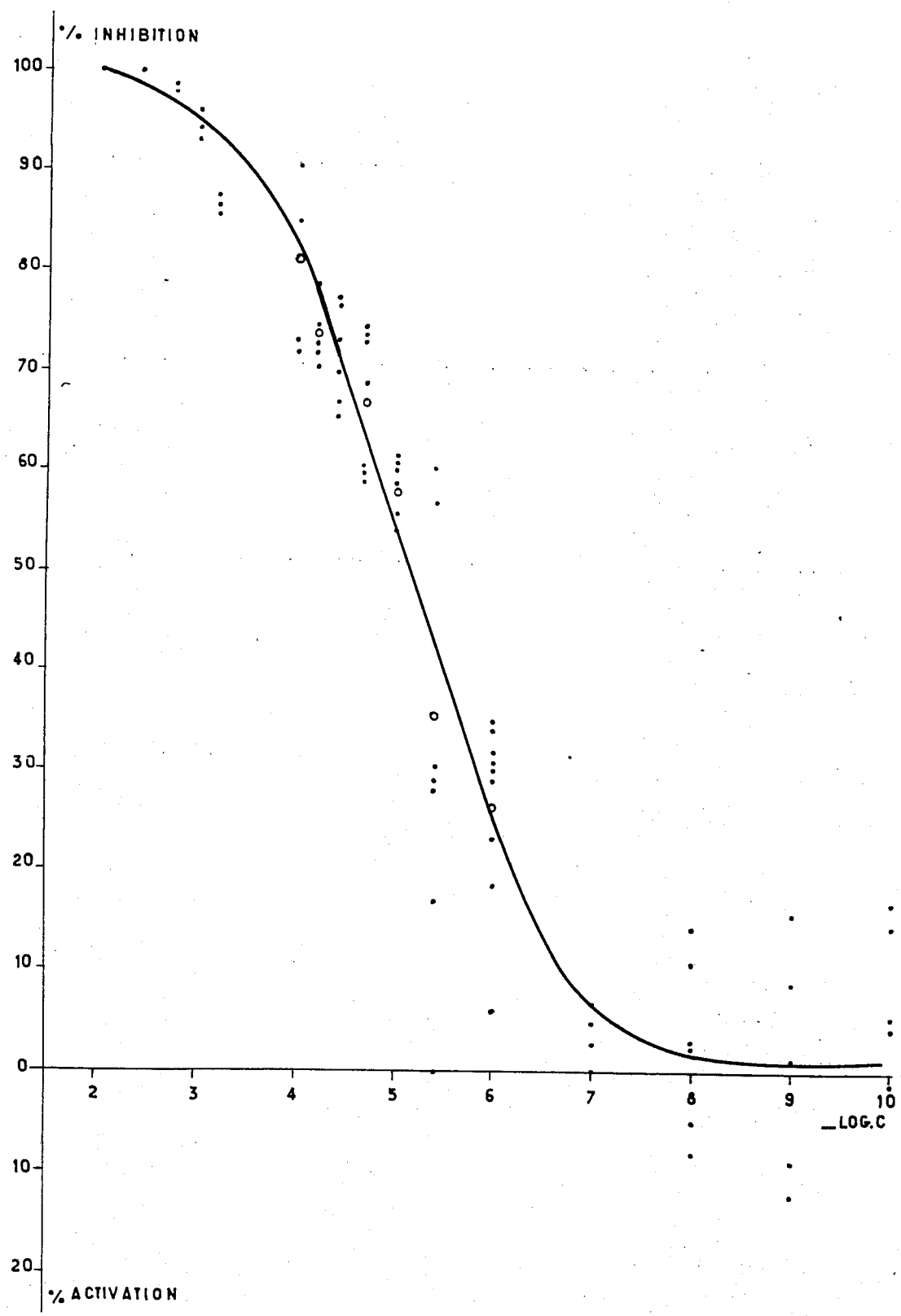

GUANYLHYDRAZONES AND MEDICAMENTS CONTAINING THEM

BACKGROUND OF THE INVENTION

The present invention relates to new guanyl hydrazones and to processes permitting their preparation, also medicaments containing them.

Numerous guanyl hydrazones have been synthesised since the preparation by Thiele of the first guanyl hydrazone, namely benzaldehyde guanyl hydrazone, at the end of the 19th century. Certain of the guanyl hydrazones described in the prior art possess a therapeutic activity, in particular the guanyl hydrazones formed from quinones and heterocyclic aldehydes. The literature describes especially the bacteriostatic and tuberculostatic activity in vitro of substituted guanyl hydrazones, such for example as the mono- and di-guanyl hydrazones of p-quinones. Bisguanyl hydrazones with a high degree of substitution have been described for their properties of combatting malaria. The bactericidal activity of 5-nitrofurfuraldehyde guanyl hydrazone has been described, and certain authors have also shown that this compound possesses a certain anti-tumoral activity in the mouse. The sympatho-mimetic action of certain bisguanyl hydrazones and of the guanyl hydrazone of p-hydroxybenzaldehyde and p-methoxy benzaldehyde has also been described. Substituted benzophenone guanyl hydrazones have been described for their analgesic, spasmolytic and anti-inflammatory activity (when one of the nuclei is substituted by a hydroxy-group) and for their anti-malarial activity (when the nuclei are substituted by one or more atoms of halogen or by groups containing halogen atoms).

The works of E. MÜTSCHLER, J. SPRINGER and O. WASSERMANN (Biochemical Pharmacology, vol. 19, pp. 9-15, Pergamon Press 1970) have shown that guanyl hydrazones of various aromatic carbonyl compounds are inhibitors of the MAO (monoamine oxydase) of guinea pig liver mitochondriae, in vitro. Finally works by SARTORELLI et coll. 1965 (reported in G. MATHE, chemotherapy of cancer (leukaemias, haematosarcomas, solid tumours), 2nd edition, Expansion Scientifique Française Ed.) have shown that methylglyoxal-bis (guanyl hydrazone) forms complexes with ADN and inhibits the synthesis of nucleic acids, and BURCK et coll. 1962 (G. MATHE, ibid. have formulated the hypothesis that it would affect cellular respiration, inhibiting lactic and malic dehydrogenases. Its action has been verified in acute myeloblastic and promyelocytary leukaemias, but it has proved less efficacious in the acute transformations of chronic myeloid leukaemia and in other leukaemias, and sometimes but rarely efficacious in Hodgkin's disease. Its administration is however accompanied by various cutaneous, digestive and metabolic troubles, in particular hypoglycaemia).

The present invention aims at providing for new guanyl hydrazones which are distinguished in particular by their therapeutic properties and especially by their antimitotic, IMAO and platelet anti-aggregant activity.

The present invention has for an object new guanyl hydrazones, characterised in that they respond to the following general formula I:

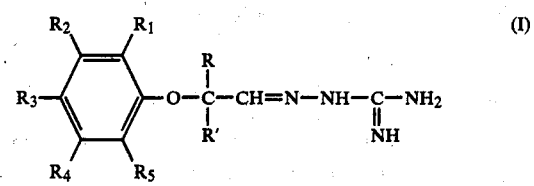

wherein:
R₁, R₂, R₃, R₄ and R₅, which may be identical or different, represent atoms of hydrogen, halogen (such as fluorine, chlorine bromine), lower alkyl groups (such as methyl, isopropyl, tert-butyl), alkoxy groups (such as methoxy), the aromatic group which can be mono- or polysubstituted by at least one atom of hydrogen, halogen, a lower alkyl or alkoxy group, and R and R', which may be identical or different, each represent an atom of hydrogen or a methyl group.

The present invention also relates to the physiologically acceptable salts of these compounds.

The present invention further has for object new medicaments, characterised in that they contain as an active constituent at least one of the guanyl hydrazones according to the present invention.

The present invention likewise has for an object a process for the preparation of these guanyl hydrazones, characterised in that they are prepared by condensation of the corresponding aldehydes or of their diethylacetal with aminoguanidine or with one of the salts of the latter.

BRIEF DESCRIPTION OF THE DRAWING

The drawing is a graph of antimitotic activity described in Experiment (2) below.

DETAILED DESCRIPTION OF THE INVENTION

For carrying out the process according to the present invention one advantageously operates as follows:

Preparation method A

An aqueous solution of 0.01 to 0.2 mol/g. of aminoguanidine sulphate in 25 to 30 ml. of water is added to a solution of 0.005 to 0.020 mol./g. of aldehyde in 5 to 75 ml. of ethanol at 95°. Heating is effected under reflux for about 4 hours. Then about 20 ml. of water are added. The precipitate is washed with water, then with ethanol, then recrystallised in water-ethanol mixtures.

Preparation method B

A sulphuric solution of 0.01 to 0.1 mol/g. of aminoguanidine sulphate in 25 to 30 ml. of 2 N sulphuric acid is added to a solution of 0.005 to 0.020 mol/g. of various acetals in 5 to 75 ml of ethanol at 95°. Heating is effected under reflux for about 4 hours, with agitation, then about 20 ml. of water are added, and drying is effected. The precipitate is washed with water, then with ethanol, then recrystallised in water-ethanol mixtures.

Preparation method C

A solution of aldehyde of 0.005 to 0.020 mol/g. in 5 to 75 ml. of ethanol is added to a solution of 0.01 to 0.2 mol/g. of aminoguanidine in 25 to 30 ml. of water. Heating is effected under reflux under a nitrogen atmosphere for about 30 hours, with agitation.

The alcohol and the water are distilled in vacuo and the residue is taken up with ether and filtered.

The precipitated guanyl hydrazone is recrystallised in isopropanol.

By the use of the one or the other of the variants of the process according to the present invention which have just been described, a certain number of phenoxyacetic acid guanyl hydrazones has been prepared. Among the new guanyl hydrazones according to the present invention thus obtained, the guanyl hydrazones listed in Table I below are given by way of non-limitative examples.

TABLE I

|    | $R_1$       | $R_2$   | $R_3$       | $R_4$   | $R_5$ | R       | R'     | m.p. °C.             |
|----|-------------|---------|-------------|---------|-------|---------|--------|----------------------|
| 1  | H           | H       | H           | H       | H     | H       | H      | 190° (sulphate)      |
| 2  | Cl          | H       | H           | H       | H     | H       | H      | 198° (sulphate)      |
| 3  | H           | Cl      | H           | Cl      | H     | H       | H      | 202° (sulphate)      |
| 4  | H           | H       | Cl          | H       | H     | H       | H      | 230° (sulphate)      |
| 5  | $CH_3O$     | H       | H           | H       | H     | H       | H      | 162° (sulphate)      |
| 6  | H           | $CH_3O$ | H           | H       | H     | H       | H      | 172° (sulphate)      |
| 7  | H           | H       | $CH_3O$     | H       | H     | H       | H      | 193° (sulphate)      |
| 8  | $CH_3$      | H       | H           | H       | H     | H       | H      | 196° (sulphate)      |
| 9  | H           | $CH_3$  | H           | H       | H     | H       | H      | 202° (sulphate)      |
| 10 | H           | H       | $CH_3$      | H       | H     | H       | H      | 208° (sulphate)      |
| 10 | H           | H       | $CH_3$      | H       | H     | H       | H      | 141° (methane sulphonate) |
| 11 | $-CH(CH_3)_2$ | H     | H           | H       | H     | H       | H      | 186° (sulphate)      |
| 12 | H           | H       | Br          | H       | H     | H       | H      | 226° (sulphate)      |
| 13 | H           | H       | F           | H       | H     | H       | H      | 240° (sulphate)      |
| 14 | $CH_3$      | H       | $CH_3$      | H       | H     | H       | H      | 215° (sulphate)      |
| 15 | H           | $CH_3$  | $CH_3$      | H       | H     | H       | H      | 210° (sulphate)      |
| 16 | H           | $CH_3$  | $CH_3$      | $CH_3$  | H     | H       | H      | 239° (sulphate)      |
| 17 | Cl          | H       | Cl          | H       | H     | H       | H      | 248° (sulphate)      |
| 18 | $-C(CH_3)_3$ | H      | H           | H       | H     | H       | H      |                      |
| 19 | H           | H       | $-C(CH_3)_3$ | H      | H     | H       | H      |                      |
| 20 | H           | H       | H           | H       | H     | $CH_3$  | H      |                      |
| 21 | H           | H       | H           | H       | H     | $CH_3$  | $CH_3$ |                      |
| 22 | $CH_3$      | H       | H           | H       | H     | $CH_3$  | H      |                      |

As well as the preceding features, the invention also includes further features which will appear from the following description.

The present invention relates more particularly to the new guanyl hydrazones described above, the processes for preparation thereof and the means adapted to the carrying out of these processes, and the medicaments containing the said guanyl hydrazones as active constituents.

The present invention can be better understood with the aid of the supplementary description which will follow, in which there will be found examples of the preparation of the guanyl hydrazones of general formula I according to the present invention, also a report of pharmacological experiments demonstrating the IMAO activity, the antimitotic activity and the platelet anti-aggregant activity of the new compounds according to the invention.

It must, however, be clearly understood that the examples which will follow, as also the report of pharmacological experiments, are given solely by way of illustration of the object of the invention and they in no manner constitute a limitation, especially as regards any further therapeutic properties which may subsequently be attributed to the new guanyl hydrazones according to the present invention.

EXAMPLES OF PREPARATION OF GUANYL HYDRAZONES OF GENERAL FORMULA I ACCORDING TO THE INVENTION

Example 1

Preparation of the guanyl hydrazone of o-chlorophenoxyacetaldehyde (sulphate)

A solution of 3.3 g of aminoguanidine sulphate in 30 ml. of water is added to a solution of 2.8 g. of o-chlorophenoxy acetaldehyde in 30 ml. of ethyl alcohol at 95°. Heating is effected under reflux for 4 hours, with addition of a few drops of acetic acid. After cooling, a solid product precipitates and it is separated and washed with very little water followed by ethanol. Recrystallisation is effected in the water-ethanol mixture (1/1). The o-chlorophenoxy acetaldehyde guanyl hydrazone is obtained in the form of sulphate, m.p.=198° C., with a yield of 90%.

Example 2

Preparation of the guanyl hydrazone of o-methoxy phenoxy acetaldehyde (sulphate)

A sulphuric solution of 2.8 g. of aminoguanidine sulphate in 25 ml. of 2 N $H_2SO_4$ is added to a solution of 3.6 g. of aldehyde in form the of diacetal in 5 ml. of ethyl alcohol at 95°.

Heating is effected under reflux for 4 hours with agitation. Then 20 ml. of water are added, and drying is effected. The precipitate is washed with water followed by ethanol.

The o-methoxy phenoxy acetaldehyde guanyl hydrazone is obtained in the form of sulphate, mp.=162° C., with a yield of 80%.

Example 3

Guanyl hydrazone of p-methyl phenoxy acetaldehyde (methane sulphonate)

A solution of aminoguanidine is prepared from 0.1 mol/g. of aminoguanidine bicarbonate in 20 ml. of water, upon which 8.5 ml. of concentrated hydrochloric acid are reacted drop by drop. After dissolution 0.1 mol./g. of soda in 10 ml. of water are added.

This aqueous solution is poured into an ethanolic solution of p-methyl phenoxy acetaldehyde kept at 0° C. (p-methyl phenoxy acetaldehyde 0.05 mol/g., ethyl alcohol at 95°:50 ml.).

Under a stream of nitrogen, heating is effected for 6 hours under reflux with agitation.

The alcohol and the water are distilled in vacuo, the p-methyl phenoxy acetaldehyde guanyl hydrazone precipitates and after shaking out and recrystallisation in isopropyl alcohol one obtains crystals of m.p.=210° C.

0.0073 mol/g. of methane sulphonic acid are added to 0.0073 mol/g. of these crystals in acetone (300 ml.), solution the major part of the acetone (200 ml.) is distilled and the methane sulphonate precipitates by addition of ether. The p-methyl phenoxy acetaldehyde methane sulphonate recrystallised in an acetone-ether mixture possesses a melting point of 141° C.

In the preceding examples the guanyl hydrazones of various phenoxy acetaldehydes were obtained either in the form of sulphates (examples 1 and 2), or in the form of methane sulphonate (example 3); however it will easily be understood that the compounds of general formula I according to the present invention can be used either in the free state or in the form of their physiologically acceptable salts, with comparable therapeutic results.

Report of Pharmacological Experiments Carried Out to Demonstrate the Therapeutic Properties of the Compounds of General Formula I The guanyl hydrazones of general formula I according to the present invention possess remarkable therapeutic properties, especially an antimitotic activity, a platelet anti-aggregant activity and an IMAO activity, as appears from the experiments carried out using guanyl hydrazones of general formula I according to the present invention.

1. I.M.A.O. activity

The inhibiting activity of the envisaged guanyl hydrazones in relation to rat liver monoaminoxydase was determined by means of a spectrophotometric method, using kynuramine as substratum.

The I.M.A.O. activity was determined for various concentrations of guanyl hydrazone. The concentrations for which one obtains 50% inhibition relate to the pI 50, which is calculated as follows:

For each concentration about ten experiments are carried out, from which the mean activity $Y_i$ is determined. Only concentrations giving a $Y_i$ between 15 and 85% of activity are retained.

Assume N concentrations $C_i$ retained; to each $C_i$ there correspond a certain number $n_i$ of experiments and a mean activity $Y_i$.

Assume in all $NT = \Sigma n_i$ experiments.

(a) The equation of the straight line $Y_i = f(C_i)$ is calculated by the method of least squares.

To this straight line there are attached different statistic tests to express its validity, as straight line only.

Then the corresponding concentration is deduced for $Y = 50\%$.

(b) Statistical calculations permit evaluation of the legitimacy of the linear model. These calculations take account of all the points, that is to say NT experiments, whereas the straight line is determined from the mean activities only, which means that these calculations take account of the dispersion which affects every average.

(c) Calculation of the confidence interval for $\alpha = 0.05$.

The pI$_{50}$s of the compounds 1 to 7 appearing in Table I above were calculated by application of the method as just described; they have been listed in Table II below:

TABLE II

| Compound | pI 50 |
|---|---|
| 1 | 4.90 |
| 2 | 4.94 |
| 3 | 4.70 |
| 4 | 4.70 |
| 5 | 4.94 |
| 6 | 5.16 |
| 7 | 4.50 |

2. Antimitotic activity (A) Inhibition of growth of vegetable cells

The test of the inhibition of the growth of the root meristem of *Lipidium sativum* was used, which test is used to evaluate the cytostatic action of series of drugs. It consists in placing germinated grains of *Lipidium sativum* in 15 ml. of aqueous solution containing 1% of methyl cellulose, in which the guanyl hydrazones are placed in suspension.

After leaving in darkness for 24 hours at the temperature of 27° C., the elongation of the root in comparison with that of a control batch (Li Lipidium sativum grain in methyl cellulose medium) is determined.

By proceeding as described for the power of inhibition of the monoamino-oxydases, and as from the concentration of guanyl hydrazones causing 50% inhibition of the root growth, one obtains the pI 50 for each of the compounds.

The calculation of the pI 50 of compound 4 was reproduced by way of non-limitative example in the graph constituting the attached single figure, which gives the percentages of inhibition of the growth of vegetable cells (*Lipidium sativum*) obtained with this compound; for this calculation the retained concentrations $C_i$, $N = 7$.

$$Y = -28.73\, C + 197.7.$$

which permits of deducing the corresponding concentration for $Y = 50\%$ namely pI $50 = 5.14$.

The validity of the linear model was evaluated with the aid of test F:

$$F^{7-2}_{56-7} = 2.375$$

(56 representing the number of experiments NT).

This test indicates that the linear model is statistically valid, since the tables give:

$$F^{7-2}_{56-7} \text{ at } 5\% = 2.4.$$

In the example supplied, for the calculation of the confidence interval for $\alpha = 0.05$, one finds:

pI $50 = 5.14 \pm 0.08$ that is to say one has five chances per hundred, if one repeats another series of measurements, of finding a pI 50 outside this limit.

The guanyl hydrazones according to the present invention, from the point of view of this test, possess pI 50s which are given for some of the compounds in Table I, in Table III below.

TABLE III

| Compound | Guanyl hydrazones pI 50 | Corresponding phenoxyacetic acid pI 50 |
|---|---|---|
| 1 | 3.16 | 3.2 |
| 2 | 3.79 | 3.95 |
| 3 | 4.47 | |
| 4 | 5.14 | |
| 5 | 3.65 | |
| 6 | 3.72 | |
| 7 | 3.99 | |
| 8 | 4.41 | 4.96 |
| 9 | 4.58 | |
| 10 | 4.23 | |
| 11 | 4.40 | |
| 12 | 5.54 | |
| 22 | — | 5.53 |

These various compounds compared with an equal molar concentration ($4.6 \cdot 10^{-3}$M) of fluoro-5 uracil show that the guanyl hydrazones cause an inhibition of the growth of the rootlets much greater than that caused by fluoro-5 uracil.

Certain of the cited examples possess a great inhibiting activity; this is the case especially with compounds 3, 4, 8, 9, 11 and 12.

A supplementary study of the activity of these products upon the inhibition of growth of animal cells was effected by tumour culture. On fibro-sarcomas induced by methyl cholanthrene (O. Flandre et coll. C.R. Jour. biol. 1966. 160 152) the products were tested: upon tumour cells in culture "in vitro" and upon treated rats.

1. upon tumour cells in culture "in vitro" the results of the tested products are reported in Table IV below, which expresses the cellular count at the 72nd hour after sub-culture, in the presence of the substances to be studied.

The results are expressed in percentage of diminution of the number of cells in comparison with the control.

The determinations were effected with the products at three molar concentrations: $10^{-4}$, $10^{-5}$ and $10^{-6}$.

TABLE IV

| PRODUCTS | MOLAR CONCENTRATIONS | | |
|---|---|---|---|
| | $10^{-4}$ | $10^{-5}$ | $10^{-6}$ |
| 1 | −15.78 | −7.89 | −5.26 |
| 2 | −15.78 | −13.15 | −7.89 |
| 3 | −31.57 | −26.31 | 0 |
| 4 | −36.84 | −23.68 | −7.89 |
| 5 | −5.26 | −2.63 | 0 |
| 6 | −18.42 | −12.63 | 0 |
| 7 | −15.78 | −15.26 | 0 |
| 8 | −10.71 | −7.89 | 0 |
| 9 | −32.14 | −13.16 | −10.5 |
| 10 | −25 | −23.68 | 0 |
| 11 | −78.57 | −42.10 | −18.42 |
| 12 | −57.14 | −40.42 | 0 |

From this table it can be seen that products 3, 4, 9, 11 and 12 in this test cause a retardation of the cellular multiplication above 30% with a concentration of $10^{-4}$ mol. Three of them still retain a certain activity at a molar concentration of $10^{-6}$.

2. Inhibiting action upon the development of a fibrosarcoma induced by methyl cholanthrene "in vivo" in the rat.

A preliminary study of products 11 and 12 has shown, after daily administration of 50 mg./kg in two doses, over three months, that the development of the tumours was clearly retarded in the treated rats, according to the weight estimations of the tumours in the treated rats and those of the untreated rats.

(B) Inhibition of growth of animal cells $B_1$ Action of the substances upon cultures of trypsinised fibroblasts Rat fibroblast cultures are concerned and the strains have been maintained for several years.

For single-layer cultivation in Roux flasks, Trypsinisation at 0.25% detaches the cells from the flask on the one hand and from one another on the other hand.

The cells are distributed in lamellated tubes at the rate of 250,000 cells per ml., where they are deposited.

The products to be tested are introduced at different dilutions, and left to act for 48 and 72 hours.

Next, the counting of the cells is effected (10 fields for 5 blades) and the results obtained are compared with control tumours which have not received the product to be tested.

Among the products tested, compound 4 (p-chloro) and compound 11 (o-isopropyl) display a percentage of inhibition in comparison with the control of the order respectively of −77% and −100% at concentrations of $10^{-4}$ M.

$B_2$ Culture in explants

This concerns rat embryo cultures kept for at least 6 months (muscle fragment). The explants are placed in culture in plasma coagulum (cock plasma). The cultures are fed with nutrient medium (Hanx + embryonary extract + decomplemented calf foetus serum). 24 hours after placing in plasma coagulum, the product to be tested is added at different dilutions. The cultures are examined on the 4th day and the counting of the number of mitoses is effected in the growth zone of the explants. The percentage of each of the phases of the mitosis is determined for the whole (mitotic index).

While the control culture possesses a mitotic index of 2.5%, the addition of substances such as compound 4 (p-chloro) and compound 11 (o-isopropyl) causes this index to pass to values respectively of 1.2 and 1.9%, which translates a significant reduction of the number of mitoses at the metaphase level.

$B_3$ Tumour culture

This concerns fibro-sarcomas induced by methyl cholanthrene according to a technique described by O. FLANDRE, I. CIURANA, J. SECCHI and M. DAMON: Reports of the Sittings of the Biology Society, Volume 160, No. 1, 1966, page 152.

The products can be tested either upon tumour cells cultivated in vitro, or upon the rat treated by tumour cell injections either in situ or by intraperitoneal injection.

The preliminary experiments carried out with the substances according to the invention, tested on tumour cells cultivated in vitro, disclose a retardation of the cellular multiplication.

Among the products tested, compound 1 and compound 4 display a percentage of inhibition in comparison with the control, of the order respectively of −25% and −45% at concentrations of $10^{-3}$ M.

(3.) Platelet anti-aggregant action

The determination of the platelet aggregability was effected according to BORN's method, using a LABINTEC aggregometer.

Firstly a platelet-rich plasma (or PRP) and next a platelet-poor plasma (or PPP or PDP) are prepared from human blood or rabbit's blood, and the apparatus is calibrated.

Then the aggregating power of the plasma (PRP) is determined in relation to the PDP in the presence and in the absence of guanyl hydrazone. Thus it is possible to determine the percentage of inhibition of platelet aggregation as a function of the concentration. The curves obtained permit of determining a pI 50. This pI 50 varies between 3 and 4 for compounds 1 to 4. These anti-aggregant activities are greater than that of adenosine at the same concentration. The results are collected in Table V below:

TABLE V

| Compound No. (same numbering as indicated in Table I) | PI$_{50}$ |
|---|---|
| 1 | 2.92 ± 0.03 |
| 2 | 3.22 ± 0.03 |
| 3 | 3.31 ± 0.04 |
| 4 | 3.25 ± 0.02 |
| 5 | 2.96 ± 0.03 |
| 7 | 2.86 ± 0.04 |
| 8 | 3.28 ± 0.05 |
| 9 | 3.16 ± 0.03 |
| 10 | 3.09 ± 0.02 |
| 12 | 3.25 ± 0.02 |
| 13 | 3.01 ± 0.02 |
| Lysine acetylsalicylate | 1.29 ± 0.04 |

(4.) Toxicity

The evaluation of the LD 50 effected in the mouse by oral administration in the form of gummous suspension leads to values of the order of 100 to 200 mg./kg. for products 1 to 4.

The guanyl hydrazones of general formula I according to the present invention can be used with advantage in human therapeutics in particular as inhibitors of monoaminoxydase, as platelet anti-aggregants, as antimitotics.

The guanyl hydrazones of general formula I according to the present invention can be administered orally, in the form of cachets, tablets, gelatin-coated pills or lozenges, rectally in the form of suppositories, parenterally in the form of injectable ampoules, sub-cutaneously or intra-muscularly, at doses between 50 and 150 mg. (jr./adult).

From the foregoing description it appears that, whatever are the manners of utilisation, realisation and application adopted, guanyl hydrazones of novel chemical structure are obtained having interesting pharmacological activities, especially IMAO, platelet anti-aggregant and antimitotic activities, whose activity/toxicity ratio permits envisaging therapeutic utilisation.

As appears from the foregoing, the invention is in no way limited the manners of utilisation, realisation and application which have just been described more explicitly; on the contrary it includes all the variants which may come to the mind of the person acquainted with the art without departing from the scope or field of the present invention.

We claim:

1. A guanyl hydrazone of the following general formula (I):

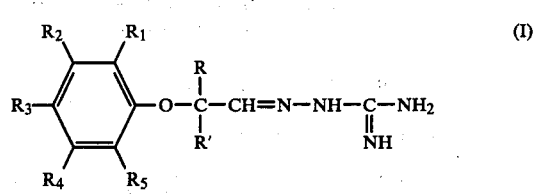

wherein:

$R_1$, $R_2$, $R_3$, $R_4$ and $R_5$, which may be identical or different, represent hydrogen, halogen, lower alkyl or alkoxy of which the alkyl is lower alkyl; and R and R', which may be identical or different, represent hydrogen or methyl, and the physiologically acceptable salts thereof.

2. The guanyl hydrazone of claim 1, wherein the alkyl of said alkoxy is methyl.

3. The guanyl hydrazone of claim 1, wherein said halogen is fluorine, chlorine or bromine.

4. The guanyl hydrazone of claim 1, wherein said lower alkyl is isopropyl or tert-butyl.

5. The guanyl hydrazone of claim 1, wherein said alkoxy is methoxy.

6. The guanyl hydrazone of claim 1, wherein said physiologically acceptable salts are sulphates or methane sulphonates.

7. The guanyl hydrazone of claim 1, wherein said guanyl hydrazone is selected from the group consisting of compounds of the general formula (I) wherein:

$R_1$, $R_2$, $R_3$, $R_4$, $R_5$, R and R' are H;
$R_1$ is Cl and $R_2$, $R_3$, $R_4$, $R_5$, R and R' are H;
$R_2$ is Cl and $R_1$, $R_3$, $R_4$, $R_5$, R and R' are H;
$R_3$ is Cl and $R_1$, $R_2$, $R_4$, $R_5$, R and R' are H;
$R_1$ is CH$_3$O— and $R_2$, $R_3$, $R_4$, $R_5$, R and R' are H;
$R_2$ is CH$_3$O— and $R_1$, $R_3$, $R_4$, $R_5$, R and R' are H;
$R_3$ is CH$_3$O— and $R_1$, $R_2$, $R_4$, $R_5$, R and R' are H;
$R_1$ is CH$_3$— and $R_2$, $R_3$, $R_4$, $R_5$, R and R' and H;
$R_2$ is CH$_3$— and $R_1$, $R_3$, $R_4$, $R_5$, R and R' are H;
$R_3$ is CH$_3$— and $R_1$, $R_2$, $R_4$, $R_5$, R and R' are H;
$R_1$ is iso-propyl and $R_2$, $R_3$, $R_4$, $R_5$, R and R' are H;
$R_3$ is Br and $R_1$, $R_2$, $R_4$, $R_5$, R and R' are H;
$R_3$ is F and $R_1$, $R_2$, $R_4$, $R_5$, R and R' are H;
$R_1$ and $R_3$ are CH$_3$— and $R_2$, $R_4$, $R_5$, R and R' are H;
$R_2$ and $R_3$ are CH$_3$— and $R_1$, $R_4$, $R_5$, R and R' are H;
$R_2$, $R_3$ and $R_4$ are CH$_3$— and $R_1$, $R_5$, R and R' are H;
$R_1$ and $R_3$ are Cl and $R_2$, $R_4$, $R_5$, R and R' are H;
$R_1$ is tert-butyl and $R_2$, $R_3$, $R_4$, $R_5$, R and R' are H;
$R_3$ is tert-butyl and $R_1$, $R_2$, $R_4$, $R_5$, R and R' are H;
R is CH$_3$— and $R_1$, $R_2$, $R_3$, $R_4$, $R_5$ and R' are H;
R and R' are CH$_3$— and $R_1$, $R_2$, $R_3$, $R_4$ and $R_5$ are H;
or
$R_1$ and R are CH$_3$— and $R_2$, $R_3$, $R_4$, $R_5$ and R' are H
or a physiologically acceptable salt thereof.

8. The guanyl hydrazone of claim 7, wherein said physiologically acceptable salt is a sulphate or a methane sulphonate.

9. The guanyl hydrazone of claim 1, wherein said guanyl hydrazone is selected from the group consisting of compounds of the general formula (I) wherein:

$R_2$ is Cl and $R_1$, $R_3$, $R_4$, $R_5$, R and R' are H;
$R_3$ is Cl and $R_1$, $R_2$, $R_4$, $R_5$, R and R' are H;
$R_1$ is CH$_3$— and $R_2$, $R_3$, $R_4$, $R_5$, R and R' are H; ;
$R_2$ is CH$_3$— and $R_1$, $R_3$, $R_4$, $R_5$, R and R' are H;
$R_1$ is iso-propyl and $R_2$, $R_3$, $R_4$, $R_5$, R and R' are H;
$R_3$ is Br and $R_1$, $R_2$, $R_4$, $R_5$, R and R' are H;
or a physiologically acceptable salt thereof.

10. The guanyl hydrazone of claim 9, wherein said physiologically acceptable salt is a sulphate or a methane sulphonate.

11. The guanyl hydrazone of claim 1, wherein $R_1$ is hydrogen.

12. The guanyl hydrazone of claim 1, wherein $R_1$ is lower alkyl.

13. The guanyl hydrazone of claim 1, wherein $R_2$ is methoxy.

14. The guanyl hydrazone of claim 1, wherein $R_3$ is methoxy.

15. The guanyl hydrazone of claim 1, wherein $R'$, $R$ and $R_5$ are hydrogen.

16. The guanyl hydrazone of claim 1 wherein $R_3$ is hydrogen, halogen lower alkyl or alkoxy.

17. A pharmaceutical composition having therapeutic properties which comprises a therapeutically acceptable carrier and in a therapeutically effective amount, to inhibit platelet aggregation a guanyl hydrazone of the following general formula (I):

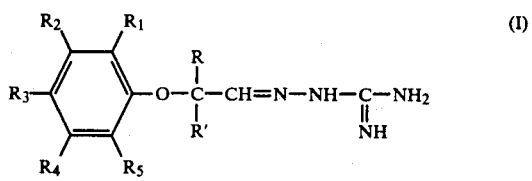

wherein:
$R_1$, $R_2$, $R_3$, $R_4$ and $R_5$, which may be identical or different, represent hydrogen, halogen, lower alkyl or alkoxy wherein the alkyl is lower alkyl; and
$R$ and $R'$, which may be identical or different, represent hydrogen or methyl,
and the physiologically acceptable salts thereof.

18. The composition of claim 17, wherein said halogen is fluorine, chlorine or bromine.

19. The composition of claim 17, wherein said lower alkyl is methyl, isopropyl or tert-butyl.

20. The composition of claim 17, wherein said alkoxy is methoxy.

21. The composition of claim 17, wherein said physiologically acceptable salts are sulphates or methane sulphonates.

22. The composition of claim 17, wherein said guanyl hydrazone is selected from the group consisting of compounds of the general formula (I) wherein:

$R_1$, $R_2$, $R_3$, $R_4$, $R_5$, $R$ and $R'$ are H;
$R_1$ is Cl and $R_2$, $R_3$, $R_4$, $R_5$, $R$ and $R'$ are H;
$R_2$ is Cl and $R_1$, $R_3$, $R_4$, $R_5$, $R$ and $R'$ are H;
$R_3$ is Cl and $R_1$, $R_2$, $R_4$, $R_5$, $R$ and $R'$ are H;
$R_1$ is $CH_3O$— and $R_2$, $R_3$, $R_4$, $R_5$, $R$ and $R'$ are H;
$R_2$ is $CH_3O$— and $R_1$, $R_3$, $R_4$, $R_5$, $R$ and $R'$ are H;
$R_3$ is $CH_3O$— and $R_1$, $R_2$, $R_4$, $R_5$, $R$ and $R'$ are H;
$R_1$ is $CH_3$— and $R_2$, $R_3$, $R_4$, $R_5$, $R$ and $R'$ are H;
$R_2$ is $CH_3$— and $R_1$, $R_3$, $R_4$, $R_5$, $R$ and $R'$ are H;
$R_3$ is $CH_3$— and $R_1$, $R_2$, $R_4$, $R_5$, $R$ and $R'$ are H;
$R_1$ is iso-propyl and $R_2$, $R_3$, $R_4$, $R_5$, $R$ and $R'$ are H;
$R_3$ is Br and $R_1$, $R_2$, $R_4$, $R_5$, $R$ and $R'$ are H;
$R_3$ is F and $R_1$, $R_2$, $R_4$, $R_5$, $R$ and $R'$ are H;
$R_1$ and $R_3$ are $CH_3$— and $R_2$, $R_4$, $R_5$, $R$ and $R'$ are H;
$R_2$ and $R_3$ are $CH_3$— and $R_1$, $R_4$, $R_5$, $R$ and $R'$ are H;
$R_2$, $R_3$ and $R_4$ are $CH_3$— and $R_1$, $R_5$, $R$ and $R'$ are H;
$R_1$ and $R_3$ are Cl and $R_2$, $R_4$, $R_5$, $R$ and $R'$ are H;
$R_1$ is tert-butyl and $R_2$, $R_3$, $R_4$, $R_5$, $R$ and $R'$ are H;
$R_3$ is tert-butyl and $R_1$, $R_2$, $R_4$, $R_5$, $R$ and $R'$ are H;
$R$ is $CH_3$— and $R_1$, $R_2$, $R_3$, $R_5$ and $R'$ are H;
$R$ and $R'$ are $CH_3$— and $R_1$, $R_2$, $R_3$, $R_4$ and $R_5$ are H;
or
$R_1$ and $R$ are $CH_3$— and $R_2$, $R_3$, $R_4$, $R_5$ and $R'$ are H
or a physiologically acceptable salt thereof.

23. The composition of claim 22, wherein said physiologically acceptable salt is a sulphate or a methane sulphonate.

24. The composition of claim 17, wherein said guanyl hydrazone is selected from the group consisting of compounds of the general formula (I) wherein:

$R_2$ is Cl and $R_1$, $R_3$, $R_4$, $R_5$, $R$ and $R'$ are H;
$R_3$ is Cl and $R_1$, $R_2$, $R_4$, $R_5$, $R$ and $R'$ are H;
$R_1$ is $CH_3$— and $R_2$, $R_3$, $R_4$, $R_5$, $R$ and $R'$ are H;
$R_2$ is $CH_3$— and $R_1$, $R_3$, $R_4$, $R_5$, $R$ and $R'$ are H;
$R_1$ is iso-propyl and $R_2$, $R_3$, $R_4$, $R_5$, $R$ and $R'$ are H;
$R_3$ is Br and $R_1$, $R_2$, $R_4$, $R_5$, $R$ and $R'$ are H;
or a physiologically acceptable salt thereof.

25. The composition of claim 24, wherein said physiologically acceptable salt is a sulphate or a methane sulphonate.

26. The composition of claim 17, wherein $R_1$ is hydrogen.

27. The composition of claim 17, wherein $R_1$ is lower alkyl.

28. The composition of claim 17, wherein $R_2$ is methoxy.

29. The composition of claim 17, wherein $R_3$ is methoxy.

30. The composition of claim 17, wherein $R'$, $R$ and $R_5$ are hydrogen.

31. The composition of claim 17 wherein in the guanyl hydrazone $R_3$ is hydrogen, halogen lower alkyl or alkoxy.

32. A method for controlling blood platelet agglutination which comprises administering, in an amount effective to control blood platelet agglutination, the pharmaceutical composition of claim 17.

33. A method of inhibiting monoaminooxydase which comprises administering, in an amount effective to inhibit the monoaminooxydase, the pharmaceutical composition of claim 17.

* * * * *